United States Patent [19]

Juhn

[11] Patent Number: 4,641,663
[45] Date of Patent: Feb. 10, 1987

[54] APPARATUS FOR COLLECTING SPECIMENS

[76] Inventor: Steven K. Juhn, 2624 Rice Creek Ter., New Brighton, Minn. 55112

[21] Appl. No.: 735,098

[22] Filed: May 17, 1985

[51] Int. Cl.⁴ .............................................. A61M 5/20
[52] U.S. Cl. .................................... 128/765; 141/27; 141/65; 604/135
[58] Field of Search ................ 128/765; 604/133, 134, 604/135; 141/27, 65

[56] References Cited

U.S. PATENT DOCUMENTS

| | | | |
|---|---|---|---|
| 2,039,177 | 4/1936 | MacKenzie | 141/27 |
| 2,098,702 | 11/1937 | Gagnon | 128/9 |
| 3,050,062 | 8/1962 | Ulmer . | |
| 3,596,653 | 8/1971 | Hotchkiss | 128/9 |
| 3,766,907 | 10/1973 | Muenzer . | |
| 3,889,682 | 6/1975 | Denis et al. . | |
| 3,911,919 | 10/1975 | Raitto . | |
| 3,957,051 | 5/1976 | Topham | 604/135 |
| 4,334,538 | 6/1982 | Juhn . | |

FOREIGN PATENT DOCUMENTS 2331319 10/1977 France ............................. 128/765
1019560 2/1966 United Kingdom .

OTHER PUBLICATIONS

"How I Do It"—Otology and Neurotology, Jun. 1981, 4 pages from the Laryngoscope, vol. XCI, No. 6, pp. 1012–1015.

Primary Examiner—Carroll B. Dority, Jr.
Attorney, Agent, or Firm—Burd, Bartz & Gutenkauf

[57] ABSTRACT

A viewer for optically inspecting the interior ear cavity having a tubular body with a passage having an open end adapted to be inserted into the ear cavity and a lens in optical alignment with the passage. A light mounted on the viewer operates to illuminate the passage and interior cavity adjacent the open inner end thereof. The viewer is used with a collector to manually collect liquid samples from the ear cavity. The collector has an elongated tube associated with a plunger that is spring biased to an out position. A releasable latch holds the plunger in an in position. When the latch is disengaged from the plunger the biasing spring moves the plunger to its out position thereby drawing fluid into the tube.

13 Claims, 11 Drawing Figures

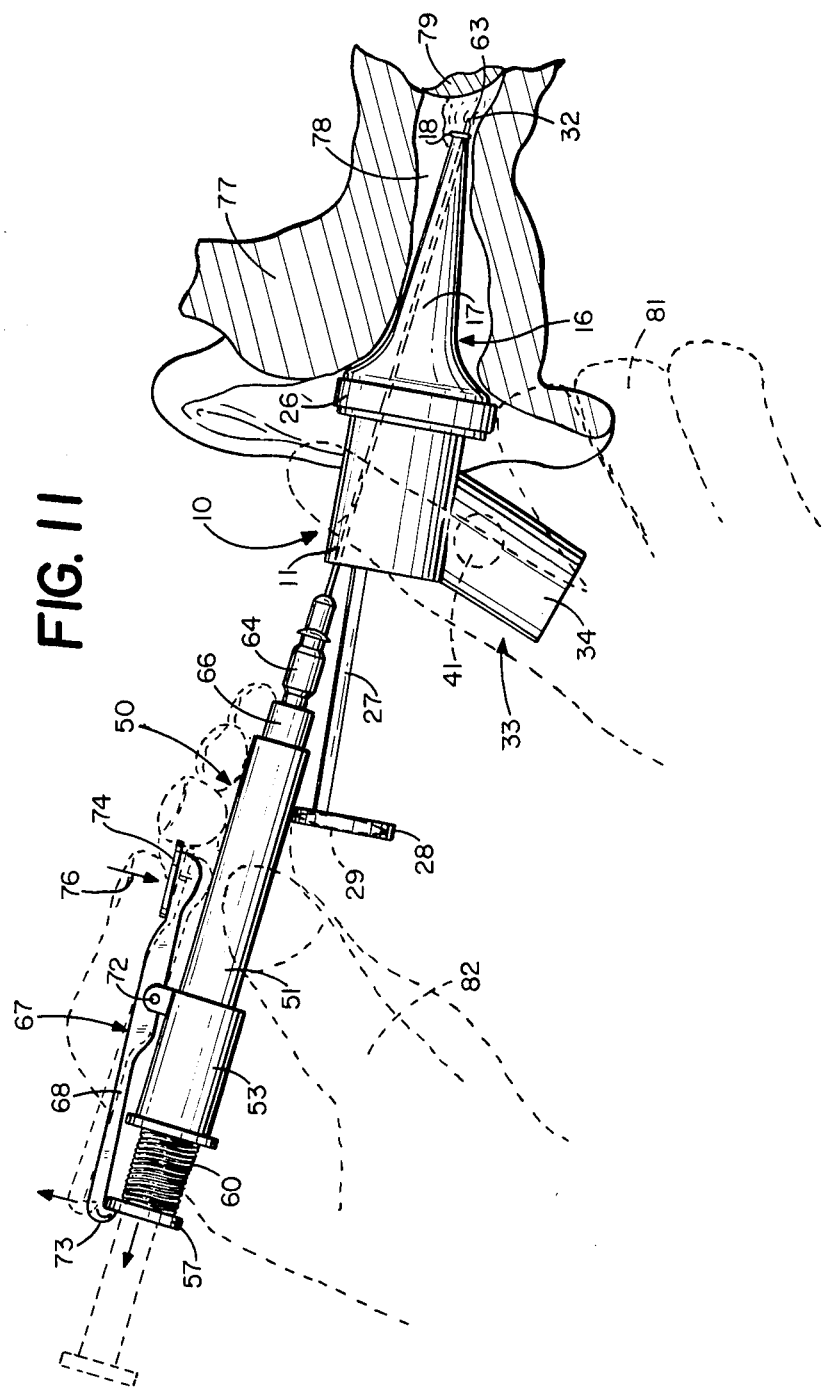

APPARATUS FOR COLLECTING SPECIMENS

FIELD OF INVENTION

The invention is in the field of instruments for inspection and collection of substances located within the interior cavities. The instrument is used to visually inspect the middle ear of a primate. A collector is used to collect liquid samples from the middle ear.

BACKGROUND OF INVENTION

Aspirators are used for collecting samples of fluids from remote cavities, such as the middle ear of a primate. The aspirators have a handle connected to a vacuum source operable to establish a vacuum pressure used to withdraw fluid from a cavity and collect the fluid in a vial attached to the handle. An example of this type of aspirator for collecting liquid samples is disclosed by Juhn in U.S. Pat. No. 4,334,538. Otoscopes having cone-shaped speculum, are used to examine the middle ear. The conventional otoscope is generally operated with two hands and is not designed to allow the examiner to withdraw material and fluid from the middle ear. The speculum supports a fixed lens which closes the outer end of the passage thereby precluding the use of instruments, such as needles or tubes, for removing a sample of fluid from the middle ear.

SUMMARY OF INVENTION

The invention is directed to a viewer used to visually examine the interior of a cavity, such as a body cavity, ear, nose, mouth, and the like with one hand. The viewer has a body with open opposite ends providing a viewing passage. A tubular member adapted to be inserted into the cavity is mounted on the body. The member has an open interior end allowing an examiner to view the interior of the cavity. A lens spaced from the body in optical alignment with the passage is supported by the body. The lens has a focal point adjacent the open end of the member adapted to be inserted into the cavity. Light generating means mounted on the body operates to illuminate the passage and interior of the cavity adjacent the open inner end of the member insertable into the cavity.

The preferred embodiment of the viewer is used to visually examine the middle ear of a primate or animal. The viewer has a body with a open passage. A cone-shaped speculum is mounted on the body. The speculum has an open inner end adapted to be positioned in the ear canal to permit the viewing of the middle ear. A lens is spaced from the body in optical alignment with its focal point adjacent the open inner end of the ear piece. Mount means supports the lens on the body. The body and ear piece have a continuous open passage which allows the examiner to utilize tools and aspirators to remove fluid from the middle ear. Light generating means mounted on the body is operable to project light into the speculum to illuminate the middle ear. This facilitates the visual examination of the middle ear. The light illuminating means includes a casing joined to the body. A lamp and battery is located within the casing. A switch mounted on the casing is operable to electrically couple the lamp and battery to turn the lamp on. A light reflector means mounted on the body directs the light toward the focal point.

The invention includes a method of viewing the middle ear chamber of a primate with one hand and collect fluid and materials therefrom with the other hand. The tubular speculum having the open longitudinal passage is positioned in the ear canal to locate the inner end thereof in the middle ear chamber. The examiner can illuminate the middle ear chamber by actuating the switch to connect the battery to the lamp. The lens enlarges the image of the middle ear chamber thereby allowing the examiner to thoroughly inspect the middle ear chamber. An apparatus for collecting fluid having an elongated tube is used to withdraw a specimen of the fluid from the middle ear chamber. The tube is inserted into the passage with the open end thereof located in the middle ear chamber. The apparatus is then operated to withdraw fluid from the middle ear chamber. The fluid is stored in a container or vial. The fluid in the chamber is analyzed for bacterialogical and biochemical study.

The apparatus for collecting fluid is a collector used to manually collect liquid samples for medical purposes from remote body cavities such as the ear, nose, throat, and mouth. The apparatus has a tubular body surrounding a chamber for holding the collected fluid. An elongated tube connected to the body has an open end and a passage in communication with the chamber. The fluid is drawn up the tube into the chamber in response to movement of a piston located in the chamber. An elongated plunger connected to the piston cooperates with a biasing means for biasing the plunger and piston to a first or out position expanding the chamber. A releasable latch mounted on the body engages the plunger to hold the plunger and piston in the second or in position. The latch is movable to disengage it from the plunger so that the biasing means will move the plunger and piston from the second position to the first position drawing fluid adjacent the open end of the tube through the tube into the chamber. The apparatus is used to collect middle ear fluids from patients who have otitis media. The fluids collected are analyzed for bacterialogical and biochemical study thereby providing information useable for appropriate diagnosis and treatment.

DESCRIPTION OF DRAWING

FIG. 11 is a diagrammatic view showing the method of utilizing the middle ear viewer and fluid collector to examine and collect the fluid from the middle ear of a primate.

DESCRIPTION OF PREFERRED EMBODIMENTS

Figure 1:
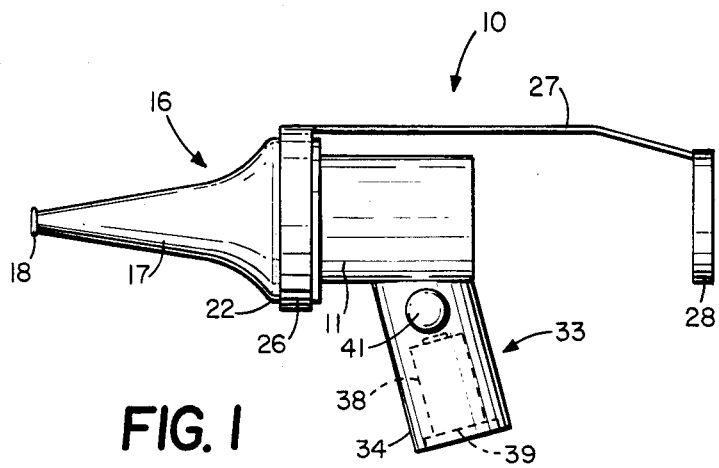
FIG. 1 is a side view of a middle ear viewer.

Referring to FIGS. 1 to 4 and 11, there is shown an otoscope 10 to visually examine an internal body cavity, such as an middle ear, nasal passage, mouth and throat and the like. The otoscope 10 is used with collector 50 to provide access to the cavity for the collection of noncontaminated fluid specimens for laboratory analysis and bacterialogical and biomedical study. Collector 50 is a hand operated device that is useable to collect body fluids, such as middle ear effusions, nasal secretions, and mouth and throat liquids. The following description is directed to the examination and collection of fluid specimens from the middle ear of humans and animals.

As shown in FIGS. 1 to 4, a middle ear viewer or otoscope 10 is used to facilitate visual examination of the tissue and tympanic membrane of the middle ear of a human and animals and fluids located therein. Viewer 10 has a cylindrical body having a linear cylindrical passage 12. Body 11 has a first end having a cylindrical flange 13 larger than body 11 and forming therewith an annular inwardly directed shoulder 14. A speculum indiated generally at 16 is removably mounted on flange 13. Speculum having different sizes and lengths can be used with body 11. Speculum 16 has an elongated generally cone-shaped tubular member 17 having a small forward end terminating in an outwardly directed annular ring 18. Ringe 18 has a round outer circumference devoid of any sharp corners or edges that can injure the ear tissue. Tubular member 17 has an annular outwardly directed lip 22 that engages flange 13 when speculum 16 is mounted on body 11. Speculum 16 has a sleeve 23 that telescopes into flange 13. The inner end of sleeve 13 engages shoulder 14 and has a internal surface generally co-extensive with the internal surface of body 11.

Figure 4:
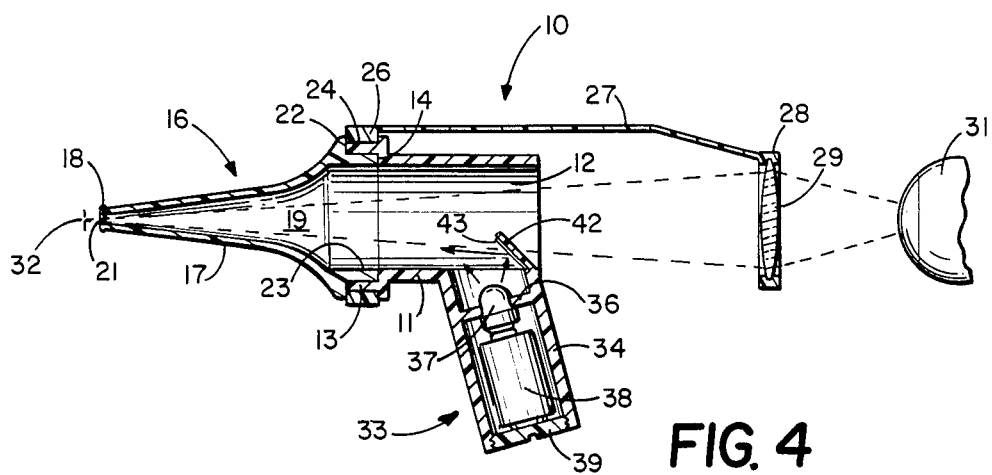
FIG. 4 is a sectional view taken along the line 4—4 of FIG. 3.

As shown in FIG. 4, body 11 and tubular member 17 have a continuous open passage from the open outside end of body 11 to the open end 21 of speculum 16. The examiner has access to the body cavity adjacent open end 21 through this continuous passage. Instruments, such as wire probes, loop probes, and the like can be manually moved through the passage to the area 32 outside of opening 21. These instruments are usable to remove substances such as ear wax from the inner ear. A fluid collector or aspirator is usable to collect middle ear fluid.

Flange 13 of body 11 has an annular groove 24 accommodating a band or annular member 26. Band 26 has a sliding relationship relative to flange 13 whereby band 26 can be rotated relative to body 11. A generally axially extended arm 27 is joined to a portion of band 26. Arm 27 is secured to a ring or lens holder 28. A convex lens 29 is retained in holder 28. Lens 29, as shown in FIG. 4, is an axial and optical alignment with opening 21. The focal point 32 of lens 29, as shown in FIG. 4, is adjacent the outside of open end 21 of ear piece 16. Lens 29 enables the examiner's eye 31 to visually inspect the tissue at focal point 32. Lens 29 enlarges the image of the tympanic membrane and identifies middle ear fluid at focal point 32. Lens 29 can be a lens assembly having a plurality of optical lenses. Lens holder 28 and lens 29 are axially spaced from the body 11 to allow fluid collectors, hereinafter described, to collect a sample of the middle ear fluid located at focal point 32. Band 26 can be rotated relative to flange 13 to circumferentially change the position of arm 27. This allows the examiner to reposition arm 27 so that it does not interfere with the use of the fluid collector or any other instrument or tool that projects into the passage 12 and 19. Lens 29 being located in concentric relation relative to band 26 remains in optical alignment with the focal area 32 so that the examiner has a continuous view of the area surrounding focal point 32.

Figure 2:
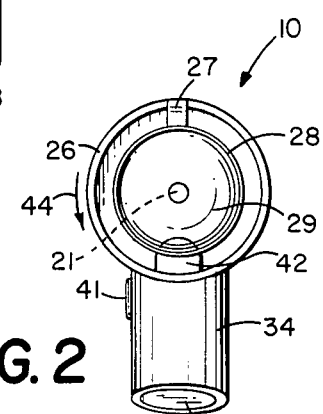
FIG. 2 is an end view of the viewing end of FIG. 1.
Figure 3:
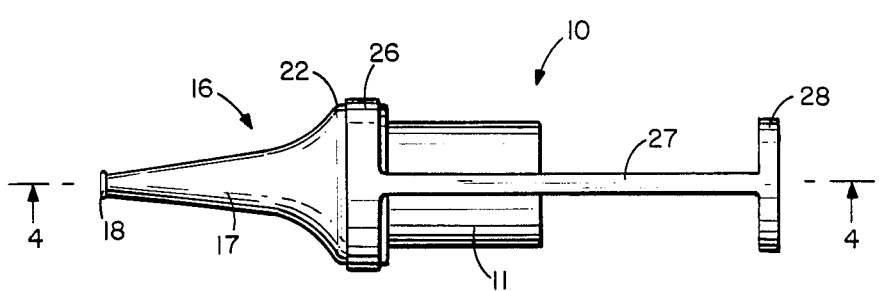
FIG. 3 is a top view of FIG. 1.

A light unit indicated generally at 33, is used to illuminate focal point 32 to enhance the visual inspection thereof. Light unit 33 has a cylindrical casing 34 integral with body 11. Casing 34 extends generally laterally from body 11 and provides a grip for the examiner. Casing 34 has an inside transverse wall 36. A light bulb or lamp 37 is mounted on wall 36. Bulb 37 is electrically connected to a battery 38 located within casing 34. Battery 38 can be a 1.4 volt dry cell battery as shown in U.S. Pat. No. 3,207,663. A removable cap or plug 39 retains battery 38 in electrical relation with lamp 37. The power source for the light bulb 37 can be remote from viewer 10. A manually operated switch 41 is operable to electrically connect battery 38 to lamp 37 to energize lamp 37. As shown in FIGS. 1 and 2, switch 41 has a manually movable actuator or button located on the side of casing 34. The button is moved into casing 34 with digital pressure to electrically connect battery 38 to the lamp 37. The light from lamp 37 is directed into passage 12. An inclined light reflector 42 is located between the lamp and the open end of body 11. Reflector 42 has an inside light reflecting surface 43 that reflects the light toward focal point 32. Reflector 42 is a tab that extends inwardly and forwardly into passage 12 from the open end of body 11.

As shown by arrow 44 in FIG. 2, band 26 can be rotated relative to body 11. This moves the arm 27 in different circumferential positions relative to casing 34. Arm 27 can be moved to positions so that it has minimum interference with the use of a fluid collecting device for removing a specimen of the fluid or wax from the area of the focal point 32. Lens 29 will remain in optical alignment with the focal point 32 so that the examiner can continue to visually inspect the focal point area during the collection of the middle ear fluid.

Figure 5:
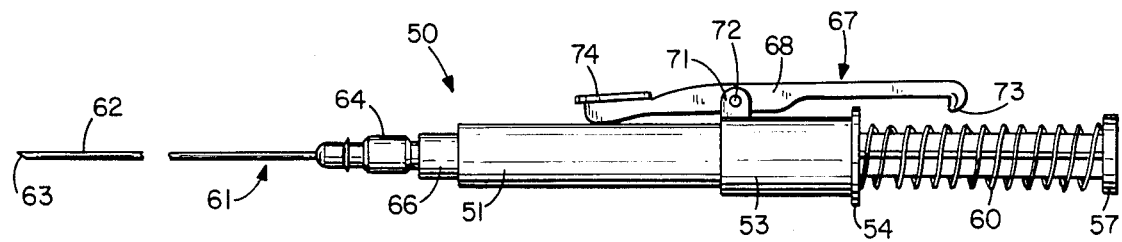
FIG. 5 is a side view of middle ear fluid collector.
Figure 6:
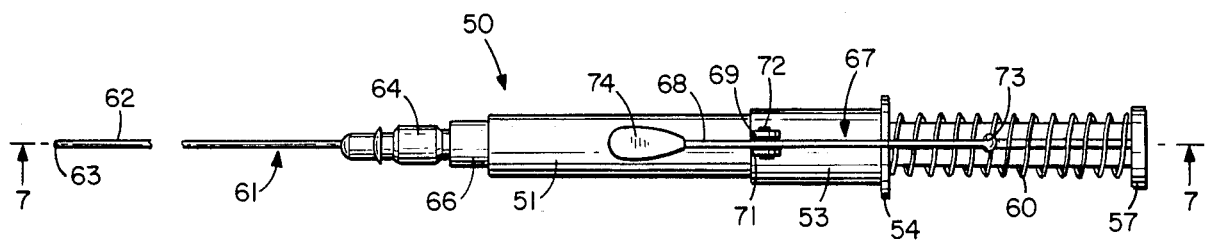
FIG. 6 is a top view of FIG. 5.
Figure 7:
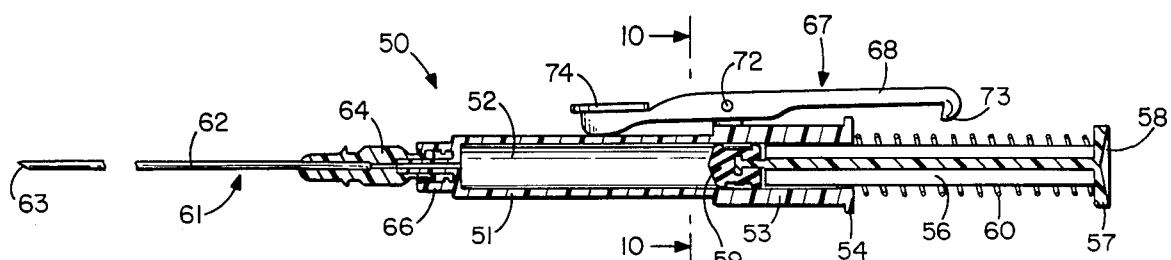
FIG. 7 is a sectional view taken along the line 7—7 of FIG. 6.

Referring to FIGS. 5 to 9, there is shown a middle ear fluid collector indicated generally at 50. Collector 50 is a self contained apparatus used to withdraw and collect a sample of fluid from the middle ear of a human for laboratory analysis. Collector 50 has a elongated cylinder or tubular body 51 having an internal cylindrical chamber 52. An open end of cylinder 51 has a cylindrical hub 53 terminating in an outwardly directed annular flange 54. A plunger 56 is slidably located within chamber 52. Plunger has a generally outer end 57 or rim having a concave recess 58. A piston 59 attached to the inner end plunger 56 is located in sliding, sealing relation with respect to the inside surface of cylinder 51. A coil spring 60 interposed between flange 54 and end 57 biases plunger 56 and piston 59 into an out position as shown in FIGS. 5 to 7.

Figure 9:
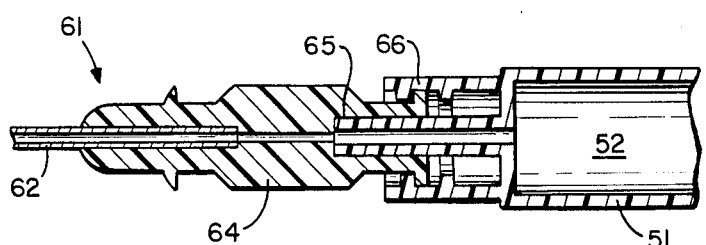
FIG. 9 is an enlarged sectional view of the needle end of the collector of FIG. 7.
Figure 10:
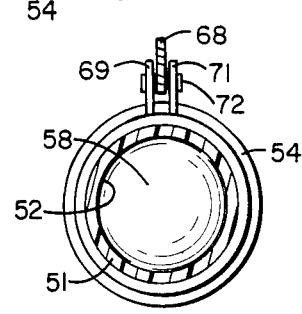
FIG. 10 is an enlarged sectional view taken along line 10—10 of FIG. 7.

A fluid pick-up tube assembly or needle unit indicated generally at 61 is releasably attached to the cylinder 51. Needle unit 61 has a passage which allows the middle ear fluid to flow into the chamber 52 when piston 59 is moved to the out position toward the open end of cylinder 51. Needle unit 61 has an elongated bendable tube 62 terminating in an end 63. Tube 62 can be an elongated bendable metal or plastic tubular member. Tube 62 has a continuous passage that is open to a passage in a connector 64. Connector 64 is releasably mounted on a female receiver 66 joined to an end of cylinder 51. Receiver 66 has a plurality of internal threads that cooperate with external threads of connector 64 to enable the use to removably mount the needle unit from receiver 66. As shown in FIG. 9, receiver 66 has a central tubular member 65 that fits into a bore in the end of connector 64. Tubular member 65 has a continuous passage open to chamber 52 and the passage of needle 63. The fluid is free to flow through the needle 63 into chamber 52 in response to a suction force in chamber 52.

Figure 8:
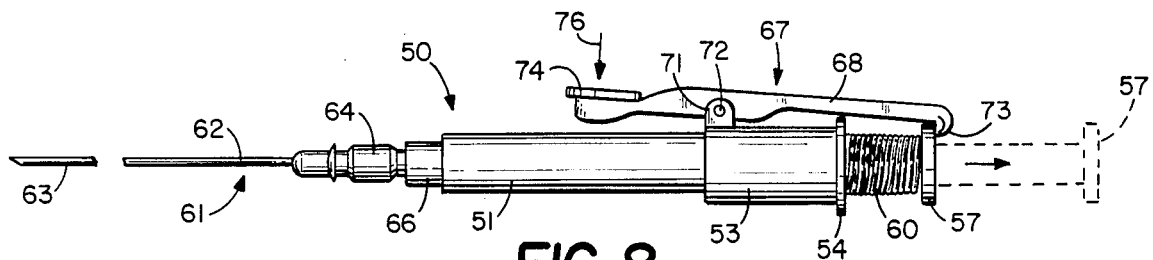
FIG. 8 is a side view similar to FIG. 5 showing the plunger held in the in position with the releasable latch.

A releasable latch indicated generally at 67 pivotally mounted on hub 53 is operable to hold plunger 56 and piston 59 in the in position as shown in FIG. 8. Latch 67 comprises a lever 68 pivotally mounted on a pair of outwardly projected ears 69 and 71 integral with hub 53. A pin 72 pivotally connects lever 68 to ears 69 to 71. Lever 68 can be integrally joined to hub 53 with a flexible connection or live hinge. Lever 68 has a inwardly directed hook 73 adapted to be located over end or rim 57 to hold plunger 56 in the in position against the biasing force of compressed spring 60. Hook 73 extends over rim 57 into tapered recess 58. The taper of recess 58 maintains hook 73 in a self-holding position on rim 57. The opposite end of lever 68 has a pad 74 having a top surface for accommodating a portion of a digit, such as an examiner's finger. Downward pressure on pad 74 is indicated by the arrow 76 in FIG. 8 will release hook 73 from end 57. The compressed spring 60 will move plunger 56 and piston 58 to an out position. This causes a suction force within chamber 52 drawing the middle ear fluid surrounding the open end 63 into chamber 52.

Referring to FIG. 11, viewer 10 is used to visually inspect the cavity and fluid in middle ear 77. Speculum 16 is located within the ear canal 78. The end 18 is located adjacent the tympanic membrane 79. Lens 29 enables the examiner to inspect the tissue and fluid or ear effusions at the focal point area 32. Viewer 10 can be used without the lens 29. Band 26 can be slipped off flange 13 when ear piece 16 has been removed from body 11. The examiner's hand 81 will grip the casing 34 and actuate switch 41. This will energize lamp 37 and illuminate the focal point 32. Lens 29 magnifies the area around focal point 32. This enables the examiner to conduct a thorough visual inspection of tympanic membrane and fluids located therein.

The middle ear viewer 10 is held between the thumb and the first finger. The thumb is located on switch actuator 41. The first finger and the remaining fingers point in the direction of ear piece 16. In use, the ends of the fingers are located in engagement with the side of the patient's head to provide accurate and stable positioning of the speculum in ear canal 78. A slight pressure between the thumb and the first finger will actuate switch 41 and thereby energizing lamp 37. The light of the lamp 37 is reflected by mirror 43 to the focal point area 32.

Fluid collector 50 is used to collect a specimen of the middle ear fluid or effusions. Collector 50 is held by the thumb and first and second fingers of hand 82. Cylinder 51 is grasped by the thumb and second finger. The first finger is located in engagement with pad 74 of the releasable latch 67. Hand 82 is moved to locate the elongated tube 62 into passages 12 and 19 of viewer 10. When the forward end 63 of the tube 62 is located in the focal point area 32 as observed through lens 29, a downward finger pressure is applied to pad 74. This rotates the lever 68 in a clockwise direction and releases hook 74 from the plunger rim 57. Spring 60 moves plunger 56 and piston 59 in a direction out of chamber 52. This establishes a suction or vacuum force in chamber 52. The middle ear fluid is drawn up tube 62 and stored in chamber 52.

The fluid stored in chamber 52 is transferred to a sterilized container or vial for transport to a laboratory for analysis. The fluid is analyzed for bacterialogical and biochemical study. Collector 50 is disposed of in an appropriate container. It is a relatively low cost device that is not intended to be reused.

Collector 50 is used in the field clinic where suction pressure is not available. Otoscope 10 is a lightweight portable instrument that has a light source and lens to provide for an effective view of the tympanic membrane of the inner ear and allows for the use of tools and collectors to accummulate a specimen of the fluid in the middle ear cavity. Otoscope 10 has a removable lens attachment 28 that allows the examiner to use it without the magnification. The light source unit 33 is integral with body 11 so that the size and weight of otoscope 10 is smaller and lighter than prior otoscopes. Lens 28, being spaced from body 11, allows the examiner to insert needles and tools through body 11 and ear piece 16 to manually collect and remove fluid from the middle ear, and materials, such as wax, that accummulate in the external ear canal.

An apparatus and method for visually inspecting the middle ear cavity and withdrawing a sample of effusions and materials therefrom has been shown and described. The viewer and collector can be employed to examine and collect fluids from other locations of the human body, such as the nose and mouth. It is understood that changes in the structure and arrangement of structure may be made by those skilled in the art without departing from the invention. The invention is defined in the following claims.

The embodiments of the invention in which an exclusive property or privilege is claimed are defined as follows:

1. An apparatus for collecting fluid comprising: a tubular body having a chamber for holding fluid, elongated tube means connected to the body, said tube means having an open end and a passage from the open end to the chamber, piston means located in said chamber, a plunger connected to the piston means for moving the piston means in the chamber, biasing means located in engagement with the plunger and body for biasing the plunger and piston means to a first position, releasable latch means mounted on the body engageable with the plunger to hold the plunger and piston means in second position, said latch means being movable to disengage the plunger whereby the biasing means moves the plunger and piston means from the second position to the first position drawing fluid adjacent the open end of the tube means through the tube means into the chamber.

2. The apparatus of claim 1 wherein: the body has a first end, a second end, and an elongated cylindrical chamber located between said ends, means mounting the tube means on said first end, said second end having an opening providing an open end of the chamber, said plunger extended through said open end and having an inner end located in said chamber, said piston means being mounted on said inner end, said plunger having an outer end, said biasing means located around said plunger between said body and outer end, said latch means comprising a lever, means movably mounting the lever on the body, said lever having a holding end releasably engageable with said outer end to hold the plunger in the second position and a release end for receiving a force to move the holding end from the inner end whereby the biasing means moves the plunger from the second position to the first position so that the piston means moves to draw fluid through the tube means into the chamber.

3. The apparatus of claim 2 wherein: said biasing means comprises a coil spring located around said plunger.

4. The apparatus of claim 2 including: a rim on the outer end of the plunger, said holding end of the lever being engageable with the rim.

5. The apparatus of claim 4 wherein: said holding end of the lever has a hook engageable with the rim to hold the plunger in the second position.

6. The apparatus of claim 5 wherein: said rim has an outer face, said face having a concave recess, said hook extending into the recess to hold the plunger and piston means in the second position.

7. The apparatus of claim 1 wherein: said biasing means comprises a coil spring located around said plunger.

8. The apparatus of claim 1 including: a rim on the outer end of the plunger, said latch having an end engageable with rim to hold the plunger and piston means in the second position.

9. The apparatus of claim 8 wherein: said end of the lever has a hook engageable with the rim.

10. The apparatus of claim 9 wherein: said rim has an outer face, said outer face having a concave recess, said hook extended into recess to hold the plunger and piston means in the second position.

11. The apparatus of claim 1 wherein: said latch means comprises a lever, means movably mounting the lever of the body, said lever having a holding end releasably engageable with said plunger to hold the plunger in the second position and a release end for receiving a force to move the holding end thereof from said plunger whereby the biasing means moves the plunger from the second position to the first position so that the piston means moves to draw fluid through the tube means into the chamber.

12. The apparatus of claim 11 wherein: said plunger has a rim on the outer end thereof, said holding end of the lever having a hook engageable with a rim to hold the plunger in the second position.

13. The apparatus of claim 12 wherein: said rim has an outer face, said face having a concave recess, said hook extending into the recess to hold the plunger and the piston means in the second position.

* * * * *